(12) United States Patent
He et al.

(10) Patent No.: US 9,255,019 B2
(45) Date of Patent: Feb. 9, 2016

(54) PROTEIN SCAFFOLDS FOR SELECTIVE ENRICHMENT OF METAL IONS

(71) Applicant: The University of Chicago, Chicago, IL (US)

(72) Inventors: Chuan He, Chicago, IL (US); Lu Zhou, Chicago, IL (US); Michael Bosscher, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 14/394,024

(22) PCT Filed: Mar. 13, 2013

(86) PCT No.: PCT/US2013/031039
§ 371 (c)(1),
(2) Date: Oct. 10, 2014

(87) PCT Pub. No.: WO2013/154731
PCT Pub. Date: Oct. 17, 2013

(65) Prior Publication Data
US 2015/0266755 A1    Sep. 24, 2015

Related U.S. Application Data

(60) Provisional application No. 61/623,154, filed on Apr. 12, 2012.

(51) Int. Cl.
*C07K 14/00* (2006.01)
*C02F 1/68* (2006.01)
*C02F 101/20* (2006.01)

(52) U.S. Cl.
CPC ............... *C02F 1/683* (2013.01); *C07K 14/00* (2013.01); *C02F 2101/20* (2013.01); *C02F 2303/18* (2013.01); *C02F 2305/00* (2013.01)

(58) Field of Classification Search
CPC ...................................................... C07K 14/00
See application file for complete search history.

(56) References Cited

U.S. PATENT DOCUMENTS

| | | | |
|---|---|---|---|
| 2003/0027302 A1 | 2/2003 | Ouadi et al. | 435/183 |
| 2003/0088083 A1 | 5/2003 | Allen et al. | 536/23.2 |
| 2011/0093964 A1 | 4/2011 | Vita et al. | 800/13 |

OTHER PUBLICATIONS

Aisen, P., Leibman, A., Zweier, J. Stoichiometric and Site Characteristics of the binding of Iron to Human Transferrin. J. Biol. Chem. 253, 1930-1937 (1978).
Bancil, L., Bertinil, I., Ciofi-Baffonil, S., Korzyreval, T., Zovo, K., Palumaa, P. Affinity gradients drive copper to cellular destinations. Nature 465, 367-368 (2010).
Regan, L., DeGrado, W. F. Characterization of a Helical Protein Designed from First Principles. Science 241, 976-978 (1988).
Lovejoy, B., Choe, S., Cascio, D., McRorie, D. K., DeGrado W. F., Eisenberg, D. Crystal structure of a synthetic triple-stranded alpha-helical bundle. Science 259, 1288-1293 (1993).
Iranzo, O., Ghosh, D., Pecoraro, V. L. Assessing the Integrity of Designed Homomeric Parallel Three-Stranded Coiled Coils in the Presence of Metal Ions. Inorg. Chem. 45, 9959-9973 (2006).
Wendt, H., Berger, C., Baici, A., Thomas, R. M., Bosshard, H. R. Kinetics of Folding of Leucine Zipper Domains. Biochemistry 34, 4097-4107 (1995).
Pordea, A., Ward, T. R Artificial Metalloenzymes: Combining the Best Features of Homogenous and Enzymatic Catalysis. Synlett. 20, 3225-3236 (2009).
DeGrado, W. F.; Summa, C. M.; Pavone, V.; Nastri, F. & Lombardi, A. De Novo Design and Structural Characterization of Proteins and Metalloproteins. Annu. Rev. Biochem. 68, 779-819 (1999).
Dutton, P. L., Moser, C. C., Engineering enzymes. Faraday Discuss. 148, 443-448 (2011).
Azoitei, M. L, Correia, B. E., Ban, Y. A., Carrico, C., Kalyuzhniy, O., Chen, L., Schroeter, A., Huang, P., McLellan, J. S., Kwong, P. D., Baker, D., Strong, R. K., Schief, W. R. Computation-Guided Backbone Grafting of a Discontinuous Motif onto a Protein Scaffold. Science 334, 373-376 (2011).
Touw, D. S., Nordman, C. E., Stuckey, J. A., Pecoraro, V. L. Identifying important structural characteristics of arsenic resistance proteins by using designed three stranded coils. Proc. Natl. Acad. Sci. 104, 11969-11974.
Matzapetakis, M., Pecoraro, V. L. Site-Selective Metal Binding by Designed Helical Peptides. J. Am. Chem. Soc. 127, 18229-18233 (2005).
Radford, R. J., Brodin, J. D., Salgado, E. N., Tezcan, A. Expanding the utility of proteins as platforms for coordination chemistry. Coord. Chem. Rev. 225, 790-803.
Lu, Y., Yeung, N., Sieracki, N., Marshall, N. M. Design of functional metalloproteins. Nature 460, 855-862 (2009).
Franczyk, T. S.; Czerwinski, K. R.; Raymond, K. N. Stereognostic Coordination Chemistry. I. The Design and Synthesis of Chelators for the Uranyl Ion. J. Am. Chem. Soc. 114, 8138-8146 (1992).
Gordon, A. E.; Xu, J.; Raymond, K. N.; Durbin, P. Rational Design of Sequestering Agents for Plutonium and Other Actinides. Chem. Rev. 103, 4207-4282 (2003).
Wegner, S. V.; Boyaci, H.; Chen, H.; Jensen, M. P.; He, C. Engineering a Uranyl-Specific Binding Protein from NikR. Angew. Chem. Int. Ed. 48, 2339-2341 (2009).
Lee, J. H., Wang, Z., Liu, J., Lu, Y. Highly Sensitive and Selective Colorimetric Sensors for Uranyl (UO22+): Development and Comparison of Labeled and Label-Free DNAzyme-Gold Nanoparticle Systems. J. Am. Chem. Soc. 130, 14217-14226 (2008).
LeClainche, L., Vita, C. Selective binding of uranyl cation by a novel calmodulin peptide. Environ. Chem. Lett. 4, 45-49 (2006).
Zeikus, J. G.; Wolee, R. S. *Methanobacterium thermoautotrophicus* sp. n., an Anaerobic, Autotrophic, Extreme Thermophile. J Bacteriol. 109, 707-715 (1972).

(Continued)

Primary Examiner — Amber D Steele
(74) Attorney, Agent, or Firm — Norton Rose Fulbright US LLP

(57) ABSTRACT

Polypeptides comprising high affinity for the uranyl ion are provided. Methods for binding uranyl using such proteins are likewise provided and can be used, for example, in methods for uranium purification or removal.

20 Claims, 12 Drawing Sheets

(56) References Cited

OTHER PUBLICATIONS

Rohwer, H., Rheeder, N., Hosten, E. Interactions of Uranium and thorium with arsenazo III in an aqueous medium. Anal. Chim. Acta 341, 263-268 (1997).

Georgiou, G., Stephens, D. L., Stathopoulos, C., Poetschke H. L., Mendenhall, J., Earhart, C. F. Display of beta-lactamase on the *Escherichia coli* surface: outer membrane phenotypes conferred by Lpp'-OmpA'-beta-lactamase fusions. Protein Eng. 9, 239-247 (1996).

Saito, K., Miyauchi, T. Chemical Forms of Uranium in Artificial Seawater. J. Nucl. Sci. Technol. 19, 145-150 (1982).

Gorden, A. E. V. et al. "Rational designs of sequestering agents for plutonium and other actinides." Chemical Reviews, vol. 103, No. 11, pp. 4207-4282 (2003).

International Search Report and Written Opinion for PCT/US2013/031039, mailed Jun. 28, 2013.

US 9,255,019 B2

PROTEIN SCAFFOLDS FOR SELECTIVE ENRICHMENT OF METAL IONS

This application is a national phase application under 35 U.S.C. §371 of International Application No. PCT/US2013/031039, filed Mar. 13, 2013, which claims the benefit of priority to U.S. Provisional Patent Application Ser. No. 61/623,154 filed on Apr. 12, 2012. The entire contents of each of the above-referenced disclosures are specifically incorporated herein by reference without disclaimer.

The invention was made with government support under Grant No. DE-FG02-07ER15865 awarded by the U.S. Department of Energy. The government has certain rights in the invention.

BACKGROUND OF THE INVENTION

1. Field of the Invention

The present invention relates generally to the field of molecular biology and bioinorganic chemistry. More particularly, it concerns protein scaffolds for selective recognition and binding of metal ions and methods for using such scaffolds.

2. Description of Related Art

Precious metals are useful in a wide variety of applications. However, they are usually found in very low concentrations in uncommon minerals. Many of the world's conventional resources are controlled by a few countries, but the ocean holds a vast opportunity for precious metal harvesting that has yet to be fully realized.

The uranyl ion ($UO_2^{2+}$), the predominant aerobic form of uranium, is present in the ocean at concentrations of 3.2 ppb (13 nM). Unique structural and electronic qualities have made selective binding of uranyl an attractive target for many studies, yet competition by various metal ions and natural ligands have limited the successful enrichment of uranyl from the ocean.

SUMMARY OF THE INVENTION

In some embodiments isolated and recombinant polypeptides are provided that specifically bind to actinide and/or lanthanide oxides, such as uranyl. Examples of such polypeptides include, without limitation, sequences at least about 80%, 85%, 90%, 95%, 96%, 97%, 98% or 99% identical to the polypeptides of SEQ ID NO: 1, 3, 5, 7 or 9 or fragments of such polypeptides having actinide oxide and/or lanthanide oxide (e.g., uranyl) binding activity.

In one embodiment a recombinant polypeptide is provided comprising an amino acid sequence at least 80%, 85%, 90%, 95%, 96%, 97%, 98% or 99% identical to SEQ ID NO: 1 (U09) wherein the amino acid sequence comprises one or more of the following features (a) an amino acid with a negatively charged side chain (e.g., Asp or Glu) at the position corresponding to Asn 13 of SEQ ID NO: 1; (b) an amino acid with a negatively charged side chain (e.g., Asp or Glu) at the position corresponding to Glu 17 of SEQ ID NO: 1; (c) an amino acid with a negatively charged side chain (e.g., Asp or Glu) at the position corresponding to Gln 64 of SEQ ID NO: 1; and/or (d) an amino acid with a polar side chain (e.g., Thr, Ser, Asn or Gln) at the position corresponding to Leu 67 of SEQ ID NO: 1. In further aspects, the amino acid sequence comprises an amino acid with a negatively charged side chain (e.g., Asp or Glu) at one or more of the position corresponding to (e) Glu 8 of SEQ ID NO: 1; (f) Glu 12 of SEQ ID NO: 1; (g) Glu 35 of SEQ ID NO: 1; and/or (h) Asp 68 of SEQ ID NO: 1. In certain aspects, a polypeptide of the embodiments comprises 2, 3, 4, 5, 6, 7 or 8 of features (a-h). For example, the polypeptide can comprise an amino acid sequence at least 85%, 90%, 95%, 96%, 97%, 98% or 99% identical to SEQ ID NO: 3 (U09"). In certain embodiments, a polypeptide according to the embodiments comprises an Asp residue at the position corresponding to Asn 13 of SEQ ID NO: 1; a Glu residue at the position corresponding to Glu 17 of SEQ ID NO: 1; a Glu residue at the position corresponding to Gln 64 of SEQ ID NO: 1 and/or a Thr residue at the position corresponding to Leu 67 of SEQ ID NO: 1. In yet further aspects, a polypeptide of the embodiments comprises the amino acid sequence of SEQ ID NO: 1 or SEQ ID NO: 3.

In a further embodiment there is provided a recombinant polypeptide comprising an amino acid sequence at least 80%, 85%, 90%, 95%, 96%, 97%, 98% or 99% identical to SEQ ID NO: 5 (U02) wherein the amino acid sequence comprises one or more of the following features: (a) an amino acid with a positively charged side chain (e.g., Arg, His or Lys) at the position corresponding to Glu 30 of SEQ ID NO: 5; (b) an amino acid with a polar side chain (e.g., Thr, Ser, Asn or Gln) at the position corresponding to Val 17 of SEQ ID NO: 5; (c) an amino acid with a negatively charged side chain (e.g., Asp or Glu) at the position corresponding to Gln 74 of SEQ ID NO: 5; and/or (d) an amino acid with a negatively charged side chain (e.g., Asp or Glu) at the position corresponding to Gln 119 of SEQ ID NO: 5. In further aspects, the amino acid sequence comprises an amino acid with a negatively charged side chain (e.g., Asp or Glu) or polar side chain (e.g., Thr, Ser, Asn or Gln) at one or more of the position corresponding to: (e) Glu 72 of SEQ ID NO: 5; (f) Gln 74 of SEQ ID NO: 5; (g) Gln 119 of SEQ ID NO: 5; or (h) Asp 121 of SEQ ID NO: 5. In certain aspects, a polypeptide of the embodiments comprises 2, 3, 4, 5, 6, 7 or 8 of features (a-h). In certain embodiments, a polypeptide according to the embodiments comprises an Arg residue at the position corresponding to Glu 30 of SEQ ID NO: 5; a Thr residue at the position corresponding to Val 52 of SEQ ID NO: 5; a Glu residue at the position corresponding to Gln 74 of SEQ ID NO: 5 and/or a Glu residue at the position corresponding to Gln 119 of SEQ ID NO: 5. In yet further aspects, a polypeptide of the embodiments comprises the amino acid sequence of SEQ ID NO: 5.

In yet a further embodiment there is provided a recombinant polypeptide comprising an amino acid sequence at least 80%, 85%, 90%, 95% or 97% identical to SEQ ID NO: 7 (U04) wherein the amino acid sequence comprises (a) a Tyr residue at the position corresponding to Phe 139 of SEQ ID NO: 7. In further aspects, the amino acid sequence comprises an amino acid with a negatively charged side chain (e.g., Asp or Glu) at one or more of the position corresponding to: (b) Asp 11 of SEQ ID NO: 7; (c) Glu 72 of SEQ ID NO: 7; and/or (d) Asp 156 of SEQ ID NO: 7. In certain aspects, a polypeptide of the embodiments comprises 2, 3, or 4 of features (a-d). In yet further aspects, a polypeptide of the embodiments comprises the amino acid sequence of SEQ ID NO: 7.

In still a further embodiment there is provided a recombinant polypeptide comprising an amino acid sequence at least 80%, 85%, 90%, 95% or 97% identical to SEQ ID NO: 9 (U10) wherein the amino acid sequence comprises one or more of the following features: (a) an amino acid with a polar side chain (e.g., Thr, Ser, Asn or Gln) at the position corresponding to Met 75 of SEQ ID NO: 9; and/or (b) an Asn residue at the position corresponding to Ser 34 of SEQ ID NO: 9. In further aspects, the amino acid sequence comprises an amino acid with a negatively charged side chain (e.g., Asp or Glu) at one or more of the position corresponding to: (c) Asp 49 of SEQ ID NO: 9; (d) Asp 53 of SEQ ID NO: 9; and/or (e) Glu 27 of SEQ ID NO: 9. In certain aspects, a polypeptide of the embodiments comprises 2, 3, 4, or 5 of the features (a-e). In certain embodiments, a polypeptide according to the embodiments comprises (a) a Ser residue at the position corresponding to Met 75 of SEQ ID NO: 9; and/or an Asn residue at the position corresponding to Ser 34 of SEQ ID NO: 9.

In some further embodiments there is provided a recombinant polynucleotide molecule comprising a nucleic acid sequence encoding a polypeptide of the embodiments. For example, the encoded polypeptide can comprise a sequence at least 80%, 85%, 90%, 95%, 96%, 97%, 98% or 99% identical to the polypeptides of SEQ ID NO: 1, 3, 5, 7 or 9. In certain aspects, the polynucleotide molecule is further defined as an expression vector wherein the nucleic acid sequence encoding a polypeptide of the embodiments is a operably linked to an expression control sequence (e.g., an expression control sequence comprising one or more element that is heterologous relative to the encoded polypeptide). An expression control sequence can be, for example, an eukaryotic, archeal or prokaryotic expression control sequence. An expression control sequence can comprise, without limitation, a promoter (e.g., an inducible promoter), an enhancer, a splice donor site, a splice acceptor site, a transcription stop signal, a polyadenylation signal, an internal ribosome entry site, or an RNA stability element.

In yet further aspects a method of manufacturing a polypeptide is provided comprising (a) expressing a polynucleotide molecule encoding a polypeptide according to the embodiments in a cell; and (b) purifying said cell and/or polypeptide. In still further embodiments, a host cell is provided comprising an expression vector of the embodiments. Examples of host cells include, without limitation, a bacterial cell, a yeast cell, a plant cell, an insect cell, a mammalian cell or a ciliate cell. In certain aspects, a polypeptide of the embodiments is expressed on the surface of the cell. In still further embodiments, the polypeptide is expressed in the intracellular space or is secreted from the cell.

In yet a further embodiment a composition is provided comprising a polypeptide of the embodiments (e.g., a polypeptide comprising a sequence at least about 80% identical to SEQ ID NO: 1, 3, 5, 7 or 9) wherein the polypeptide is immobilized on a support. For example, the polypeptide can be covalently attached to a support (e.g., via a thioester bond) or can be attached by a noncovalent association (e.g., a biotin-avadin interaction). A support of the embodiments can include, without limitation, a cell (e.g., a cell expressing the polypeptide), a bead, a column or a filter matrix, such as in a cartridge filter.

In a yet a further embodiment there is provided a method for binding uranyl comprising: (a) contacting a solution comprising uranyl with a polypeptide of the embodiments, thereby binding the uranyl to the polypeptide. In still further embodiments a method can be defined as a method for purifying or concentrating uranium comprising: (a) contacting a solution comprising uranyl with a polypeptide of the embodiments; and (b) purifying or concentrating the polypeptide thereby purifying or concentrating uranium.

A skilled artisan will recognize that such methods can be used to purify uranium (e.g., uranyl ion) as well as to reduce the level of uranium in a solution (e.g., for environmental remediation). Thus, in some embodiments, a method is provided for reducing the level of uranium in a solution comprising: (a) contacting a solution comprising uranyl with a polypeptide comprising an amino acid sequence at least 80%, 85%, 90%, 95%, 96%, 97%, 98%, 99% or more identical to SEQ ID NO: 1, 3, 5, 7 or 9, thereby binding the uranyl to the polypeptide; and (b) purifying the polypeptide away from the solution thereby reducing the level of uranium in the solution. For example, the polypeptide can be bound to a solid support, such a filter matrix. In some aspects, a method of the embodiments comprises pumping a solution past a polypeptide (e.g., through a filter matrix with a polypeptide bound thereto).

In certain aspects, a solution of the embodiments comprises uranyl having a $^{238}$U, $^{235}$U or $^{233}$U uranium isotope. Examples of solutions for use according to the embodiments include, without limitation, salt water (e.g., sea water), fresh water (e.g., river water), treated or untreated sewage, mine effluent (e.g., from tailing pools) and cooling water from nuclear reactors and/or fuel rod cooling ponds. In certain aspects, a solution of the embodiments comprises carbonate.

Certain aspects of the embodiments concern uranyl binding polypeptides of the embodiments and methods for binding uranyl with such polypeptides. For example, in certain aspects a polypeptide of the embodiments binds to uranyl with a $K_D$ of between about 100 nM and about 0.1 fM, between about 100 nM and about 0.1 fM or between about 1.8 nM and about 1.0 fM. In yet further aspects, the polypeptide binds to uranyl with a $K_D$ of less than 0.1 fM such as a $K_D$ of between about 0.1 fM and 1,000, 100, 10 or 1 zeptomolar.

In still further aspects, a method of the embodiments further comprises isolating or concentrating the polypeptide bound to uranyl. For example, the polypeptide can be purified by an affinity tag, by sedimentation (e.g., centrifugation) or by immobilization on a support. In yet further aspects, provided methods comprise eluting uranyl from the polypeptide. For example, the uranyl can be eluted by contacting the polypeptide and bound uranyl with an elution solution (e.g., a solution comprising carbonate), by heating the polypeptide, by denaturing the polypeptide, or by cleavage of the polypeptide. In still further aspects, methods of the embodiments can comprise use of a uranyl-binding polypeptide in two or more cycles of uranyl binding and elution of uranyl. For example, in some aspects, a method the embodiments comprises: (a) contacting a solution comprising uranyl with a polypeptide of the embodiments, thereby binding the uranyl to the polypeptide; (b) purifying the polypeptide away from the solution; (c) eluting the uranyl from the polypeptide; and (d) repeating steps (a)-(c) one or more times (e.g., 2, 3, 4, 5, 6, 7, 8, 9 or 10 timers). In certain aspects, eluting the uranyl from the polypeptide comprises denaturing the polypeptide. Accordingly, in some aspects, methods of the embodiments comprise renaturing (or refolding) a polypeptide of the embodiments, such as by incubation of the polypeptide in an aqueous buffer, at a neutral pH, and/or at approximately room temperature.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

Figure 1:
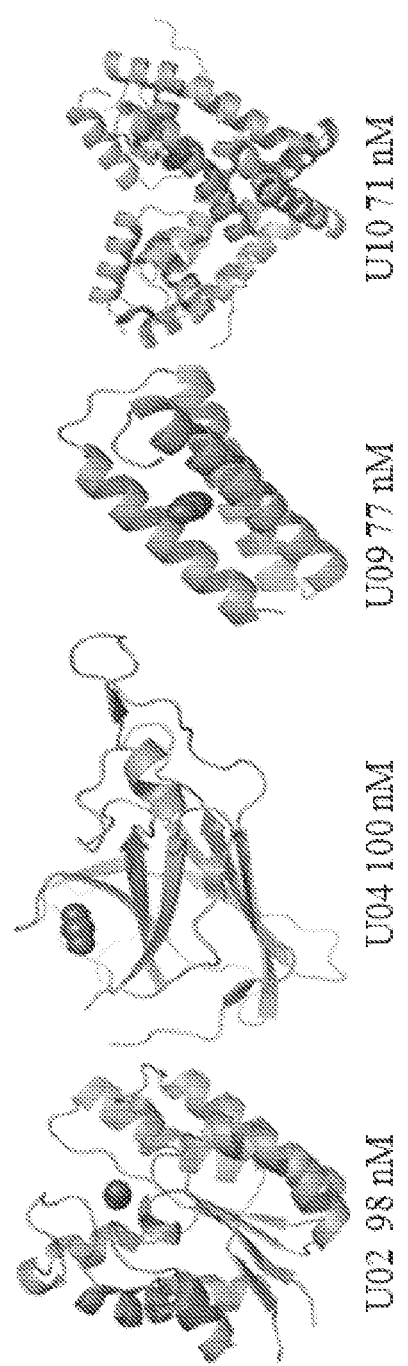
FIG. 1. Schematic shows the binding motifs for several uranyl selective metalloproteins along with their $K_D$. U09 was selected for elaboration due to probable structural stability and accessibility of beneficial mutations.

Through billions of years of evolution nature has produced strategies to recognize beneficial or toxic metal ions with high sensitivity and selectivity. Such evolved proteins are promising candidates for selective binding of trace metals for selective concentration or removal of such metals. However, even highly evolved proteins typically lack sufficient stability, affinity and selectivity to be employed in industrial scale metal purification or remediation.

Proteins disclosed herein provide for the first time highly stable and selective platforms for actinide or lanthanide oxide binding. In particular, proteins detailed here show exquisite selectivity for uranyl ion. The engineered proteins form a well-folded protein scaffold and, with the assistance of second sphere interactions, metal ions such as uranyl can be recognized well into the femtomolar ($10^{-15}$) range with extremely high selectivity. Such affinities and selectivities are sufficient for mining uranium and other elements from seawater economically or for remediation from polluted environmental sites. Additionally, proteins may be displayed on the surfaces or expressed inside of living organisms, thus allowing regeneration of these systems biologically for enrichment or remediation purposes.

II. Polypeptides

Embodiments of the invention provide isolated and recombinant polypeptides that specifically bind to actinide and/or lanthanide oxides. In particular polypeptides are provided that specifically bind uranyl. The engineered polypeptides provided herein are representative of a wide array of modified coding sequence that can be generated while maintain or even optimizing uranyl binding.

Thus, in some embodiments, a polypeptide of the embodiments comprises a sequence at least about 80%, 85%, 90%, 95%, 96%, 97%, 98% or 99% identical to the polypeptides of SEQ ID NO: 1, 3, 5, 7 or 9 having uranyl binding activity. For example, a polypeptide can comprise 1, 2, 3, 4, 5, 6, 7, 8, 9, 10, 11, 12, 13, 14, 15, or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185 or 186 contiguous amino acids, or any range derivable therein, of SEQ ID NOs: 1, 3, 5, 7 or 9.

Likewise, aspects of the embodiments concern fragments of SEQ ID NO: 1, 3, 5, 7 or 9, such as fragments having actinide oxide and/or lanthanide oxide (e.g., uranyl) binding activity. For example, a polypeptide of the embodiments can comprise 1, 2, 3, 4, 5, 6, or more segments of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185 or 186 amino acids of SEQ ID NOs: 1, 3, 5, 7 or 9. In some embodiments, a polypeptide of the embodiments comprise 1, 2, 3, 4, 5 or more repeated sequences each of which have individual uranyl binding activity.

Methods for making deletions or substitutions in polypeptide while maintaining function (e.g., uranyl binding affinity) of the polypeptide are well known in the art. For example, amino acid substitutions can be made at one or more positions wherein the substitution is for an amino acid having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in a uranyl binding protein such as those provided by SEQ ID NOs: 1, 3, 5, 7 or 9 and will likely only have minor effects on their binding affinity. As detailed in U.S. Pat. No. 4,554,101, incorporated herein by reference, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the uranyl binding polypeptides described herein may be modified by the substitution of an amino acid, for different, but homologous amino acid with a similar hydrophilicity value. Amino acids with hydrophilicities within +/−1.0, or +/−0.5 points are considered homologous.

Further guidance as to deletions or substitutions for polypeptides of the embodiments can be provided by their structure. Thus, changes can be made that would be predicted to have little or no effect on the structure of the folded polypeptide of SEQ ID NOs: 1, 3, 5, 7 or 9 (see, e.g., FIG. 1).

For example, in the case of a uranyl binding protein with an alpha-helical base structure such as U09 (SEQ ID NO: 1) and U09"(SEQ ID NO: 3). Uranyl-binding residues (Asp and Glu) are positioned by alpha helices or alpha helix bundles. Alpha helix bundles form from 3 or more alpha helices that have i and i+4 residues as hydrophobic residues to help packing and stabilization of the bundle between different helices. Thus, well positioned Asp or Glu can be designed to bind uranyl at the equatorial plane in order to provide a pentagonal bipyramidal or hexagonal bipyramidal coordination geometry to chelate the central uranyl (the axial ligands are two oxo of uranyl), see e.g., FIGS. 4 and 7. 4-6 ligands on the equatorial plane can come from Asp or Glu well positioned in the polypeptide. Furthermore, residues such as Lys, Arg, Asn, or Gln can be designed to form hydrogen bonds to the two oxo ligands of uranyl to enhance binding sensitivity and selectivity.

Further rational design of proteins has focused on the design of helical bundles (3) and coiled coils (4-6). Although many of the early applications were to mimic existing proteins, entirely new activity can be introduced into protein scaffolds as well (7-10). Coordination chemistry of a metal with organic ligands as detailed above can inform the design when biological ligand data is absent (11-12). Selective metal binding sites may also be designed by screening naturally occurring folds in structurally defined proteins for the appropriate ligation geometries (13-14).

Where a protein is mentioned herein, it is preferably a reference to a native or recombinant protein. The protein may be isolated directly from the organism of its origin or produced by recombinant DNA techniques, as outlined below.

III. Polypeptide Production

The present embodiments describe polypeptides and fragments thereof having uranyl binding activity. Recombinant DNA technology may be employed wherein a nucleotide sequence which encodes a polypeptide of the embodiments is inserted into an expression vector, transformed or transfected into an appropriate host cell and cultivated under conditions suitable for expression.

One embodiment of the invention includes the use of gene transfer to cells, including microorganisms, for the production and/or presentation of polypeptides. The gene for the polypeptide or peptide of interest may be transferred into appropriate host cells followed by culture of cells under the appropriate conditions. The generation of recombinant expression vectors, and the elements included therein, are well known in the art and briefly discussed herein. Alternatively, the protein to be produced may be an endogenous protein normally synthesized by the cell that is isolated and purified.

Host cells for expression of polypeptides can be chose from, for example, eukaryotic, bacterial or archeal host cells. In general host cells are chosen based on their cost and protein production capacity. However, in some instance, the host cell may is self be used in uranyl purification and/or bioremediation activity. In such aspects, cells may be chosen based on the environmental conditions that are requisite for their growth. Additionally, a host cell may be chosen that modulates the expression of the inserted sequences, or that modifies and processes the gene product in the manner desired. Such modifications (e.g., glycosylation) and processing (e.g., cleavage) of protein products may be important for the function of the protein or proper display of the polypeptide. Different host cells have characteristic and specific mechanisms for the post-translational processing and modification of proteins. Thus, appropriate cell lines or host systems can be chosen to ensure the correct modification and processing of the foreign protein expressed.

In specific embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference.

IV. Nucleic Acids

In certain embodiments, the present invention concerns recombinant polynucleotides encoding the polypeptides of the embodiments. As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, or more nucleotides, nucleosides, or base pairs, including all values and ranges therebetween, of a polynucleotide encoding one or more amino acid sequence described or referenced herein (e.g., SEQ ID NOs: 2, 4, 6, 8 or 10). It also is contemplated that a particular polypeptide may be encoded by nucleic acids containing variations having slightly different nucleic acid sequences but, nonetheless, encode the same or substantially similar protein.

In particular embodiments, isolated nucleic acid segments and recombinant vectors are provided incorporating nucleic acid sequences that encode a variant uranyl binding protein. The term "recombinant" may be used in conjunction with a polynucleotide or polypeptide and generally refers to a polypeptide or polynucleotide produced and/or manipulated in vitro or that is a replication product of such a molecule.

The nucleic acid segments used in the present embodiments can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy.

As discussed above, a tag or other heterologous polypeptide may be added to the modified polypeptide-encoding sequence, wherein "heterologous" refers to a polypeptide that is not the same as the modified polypeptide.

A. Vectors

Polypeptides of the invention may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a variant SpA polypeptide the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

The particular promoter that is employed to control the expression of peptide or protein encoding polynucleotide of the invention is not believed to be critical, so long as it is capable of expressing the polynucleotide in a targeted cell, such as a bacterial cell.

2. Selectable and Screenable Markers

In certain embodiments of the invention, cells containing a nucleic acid construct of the present invention may be identified in vitro or in vive by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, plant cells, algae cells, ciliates and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (see the world wide web at atcc.org).

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

V. Uranyl Binding

Embodiments of the invention also provide a method and apparatus for the removal of uranyl from water. In certain embodiments, such an apparatus (method) may comprise filters packed with a polypeptide of the embodiments. In some cases, filters may be removable cassettes that could be easily replaced when uranyl binding capacity of the filter matrix is exhausted. For example, polypeptides of the embodiments could be used as the filter matrix in a variety filter types such as those described in U.S. Pat. Nos. 6,843,912, 6,841,066, 6,779,411, 6,328,777, D501,912, or D451,602, all incorporated herein by reference.

In certain further embodiments, water may be passed through other types of filters either before or after uranyl removal to reduce or purify other solutes or contaminates in the water, for example other filter matrices can be used for purification of metal ions, such as rare earth metals. Some examples of filters for removal of biological contaminants are found in U.S. Pat. Nos. 6,872,303 and 6,852,224, incorporated herein by reference.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Screen Identifying Protein Scaffolds for the Uranyl Ion

Uranyl binding motifs are well known and offer distinctive handholds for rational design of proteins. Uranium is a unique metal among the lanthanides and actinides, preferring to oxidize to +6 while many of the other metals remain in the +3 oxidation state. Uranium in the +6 oxidation state recruits two axial oxo ligands, forming a linear triatomic ion with an overall charge of +2 (uranyl). The ability to afford five or six equatorial ligands in pentagonal or hexagonal bipyramidal geometries separates uranyl from most of the alkali, alkaline, and transition metals. The presence of the oxo ligands distinguishes uranyl from most known lanthanide and actinide species in the environment (15, 16). Although some uranyl binding motifs have been discovered in organic ligands, in DNA, and in proteins (17-19) none have been able to cross the affinity threshold to compete with carbonate (2.2 mM in ocean) and the selectivity requirement over other metals in seawater. The distinctiveness of the uranyl ion, the utility of uranium, and the lack of an economic approach make uranyl an ideal proof of concept for rational design of selective-binding proteins.

To identify candidate uranyl binding polypeptides the protein databank (PDB) was screened for pockets that could accommodate the hexagonal bipyramid or pentagonal bipyramid uranyl binding geometries, either natively or through mutation of potential ligand residues to aspartate or glutamate. From this initial screen thousands of hits were identified and were narrowed down to ten selected candidates, each was cloned, expressed, purified, and tested for uranyl binding. Of the nine proteins that expressed well, four had $K_D$s (dissociation constant) in the range of 100 nM and below (see e.g., FIG. 1).

Example 2

Elaboration of Thermophile Hit U09

Figure 2:
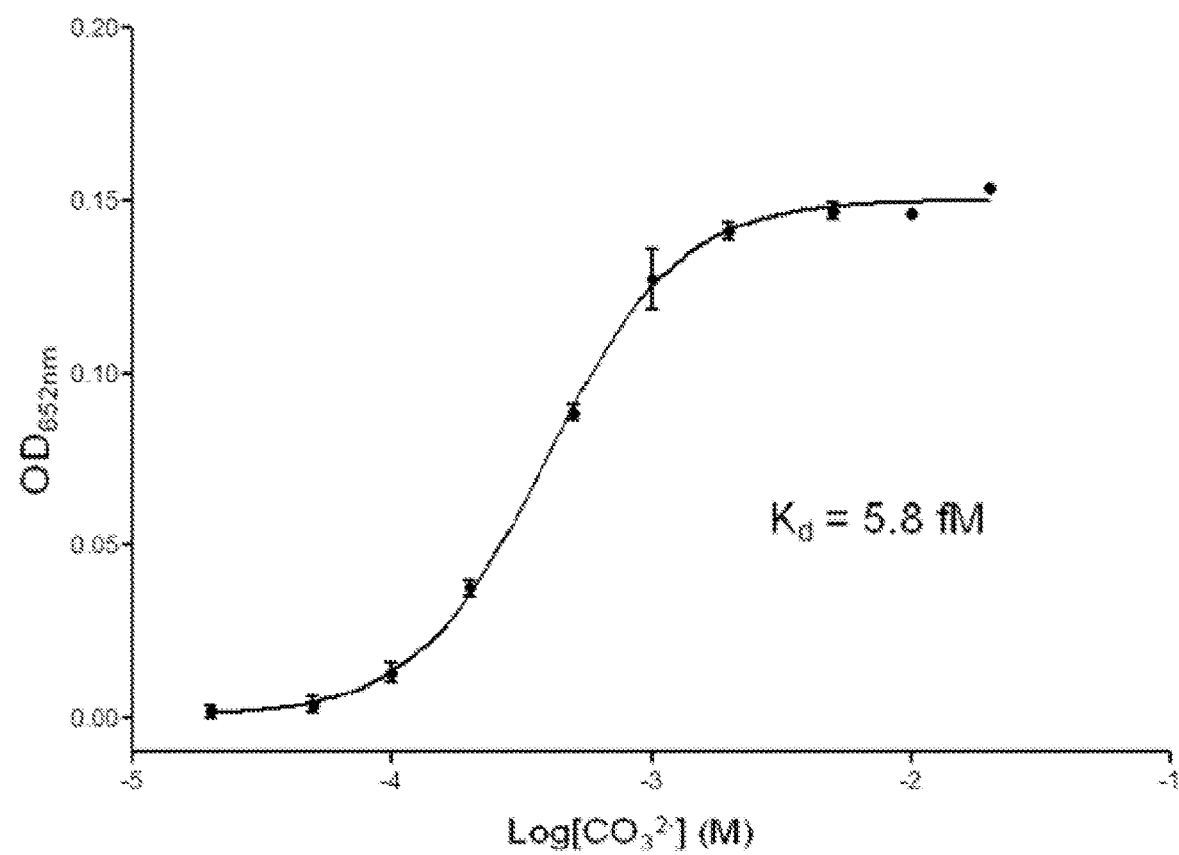
FIG. 2. Graph shows the results of a carbonate competition assay for U09".

One of the hits stood out above the others in its potential stability and utility. This small unnamed protein is from *Methanobacterium thermoautotrophicum*, an anaerobe isolated from sewage sledge in Urbana, Ill. This protein consists of three α-helices in a tight bundle (PDB accession 2PMR) and thermally stable at room and elevated temperatures. Based on the reported structure, mutations of Lys13Asn and Asn17Glu were introduced in the initial in silico screen. The mutant protein was cloned, expressed and purified, which exhibited a modest binding affinity to uranyl with a $K_D$ of 77 nM (U09). After crystallizing this construct, mutations were designed that may increase the binding affinity of U09. While a modest increase in binding affinity was achieved ($K_D$=1.8 nM) by mutating a nearby leucine to threonine (Leu67Thr) to further stabilized the structure, further mutations of a nearby glutamine to glutamate (Gln64Glu. U09') and Asn13 (originally Leu13) to aspartate (Asn13Asp) lead to an increase in $K_D$ of almost $10^9$ fold to 5.8 fM ($5.8 \times 10^{-15}$ M, FIG. 2).

Example 3

Characterization of U09"

Figure 3:
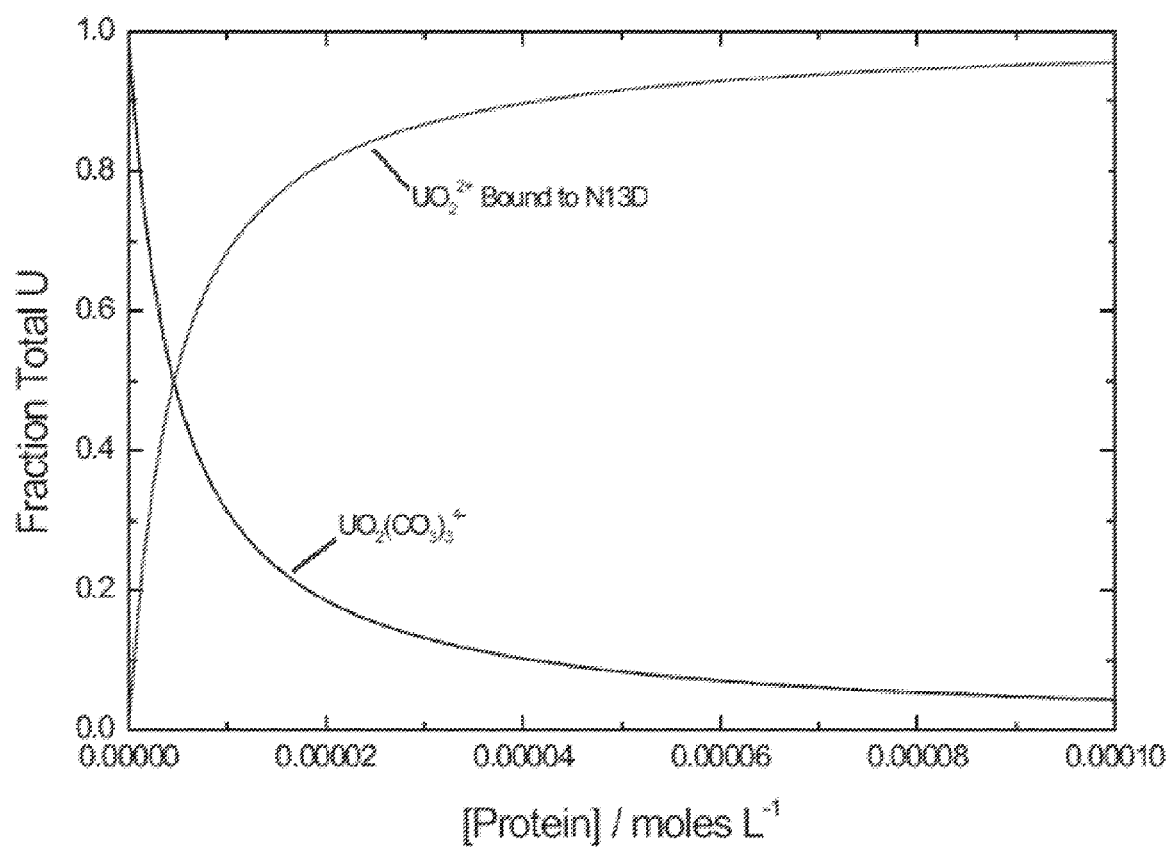
FIG. 3. Graph shows calculated uranyl binding for U09" in pH 8.15 seawater with 2.0 mM carbonate. The x-axis refers to the concentration of U09" in solution. The y-axis refers to the fraction of total uranium that has speciated a given way—either to $UO_2(CO_3)_3^{4-}$ or to $UO_2$-U09". As protein concentration increases, U09" is capable of enriching most uranyl from sea water. For example, at U09" concentrations of 60 µM or greater, over 90% of uranium speciates to the protein.
Figure 4:
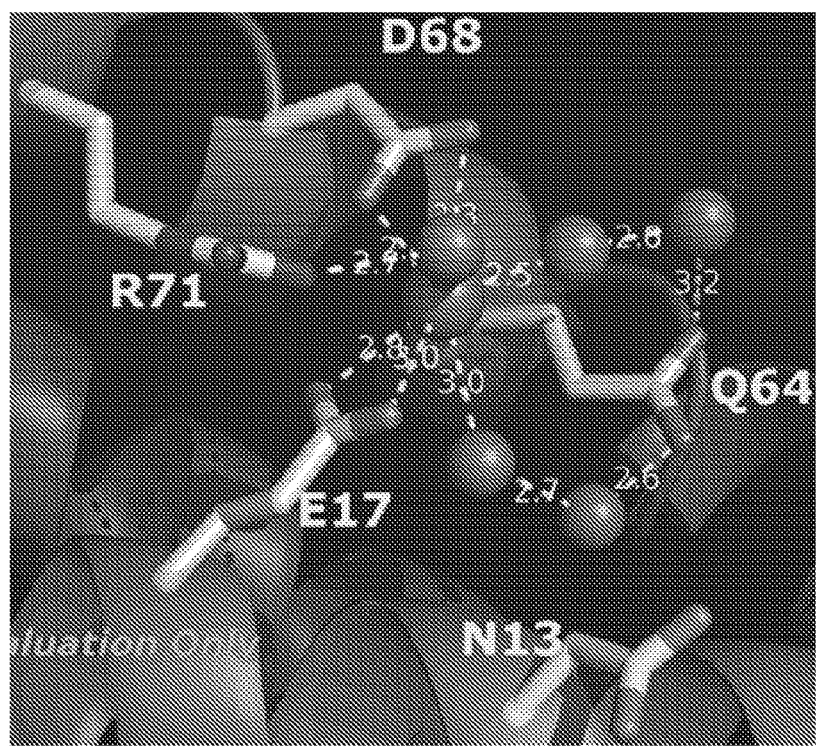
FIG. 4. Representation of a U09" crystal structure. 2% v/v Tacsimate 4.0 0.1M, Sodium acetate trihydrate pH 4.6, 16% w/v Polyethylene glycol 3,350. D68, E17, and water provide the equatorial ligand sphere in this structure. Uranyl oxo ligand is stabilized by hydrogen-bond donation from R71.
Figure 5:
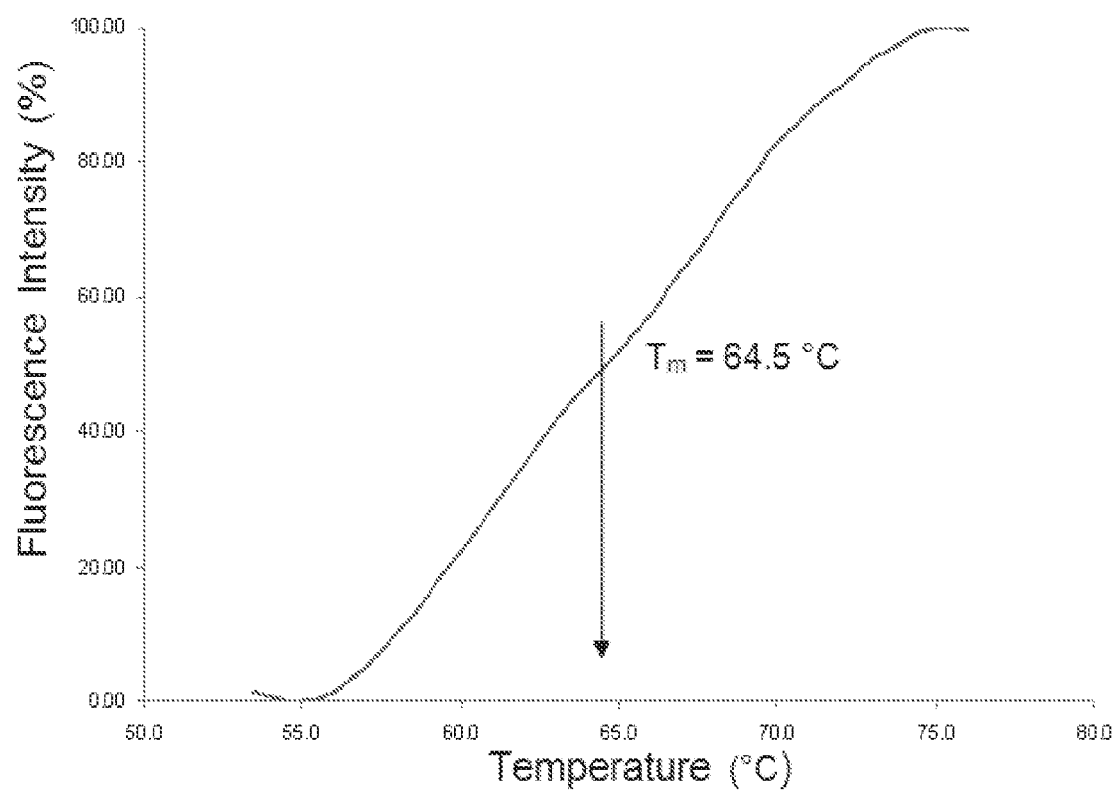
FIG. 5. Graph demonstrates that U09" has a high thermal stability, with a Tm of 64.5° C.
Figure 6:
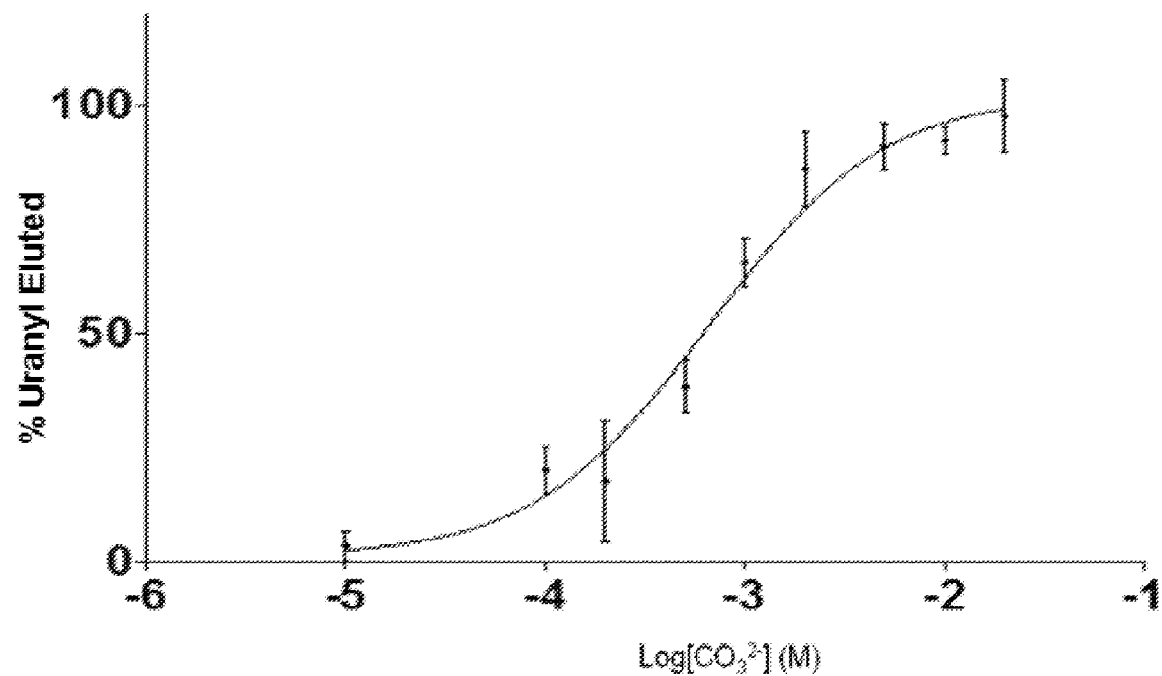
FIG. 6. Graph shows results of a U09' carbonate competition assay. The peak is broader than would be expected, indicating potential multiple unique binding events.

The new construct comprising Asn13Asp/Gln64Glu/Leu67Thr mutations was named U09". The affinity of U09" ($K_D$ 5.8 fM) is high enough to remove much of the uranium from sea water at moderate concentrations (FIG. 3). Based on data fitting analysis, at 20 µM U09" should extract 80% of the total uranyl from sea water and 60 µM U09" should extract over 90%. The structure of U09" with bound uranyl was solved (FIG. 4). As initially designed, E17 and D68 serve as axial ligands, while R71 donates a hydrogen bond to the uranyl oxo ligand. Although the L67T was designed to introduce a hydrogen bond to the other uranyl oxo ligand, instead it simply served to further stabilize the structure. Similarly, N13D and Q64E mutations were intended to introduce another bidentate ligand to the uranyl equatorial field, but seem to also stabilize the structure through indirect interactions. It is possible that at high pH one or both of the carboxylates would interact directly with the uranyl, but new crystallization conditions must be found at higher pH to elucidate all interactions. In addition to very high affinity, U09" has an excellent thermostability with a Tm of 64.5° C. (FIG. 6). U09" can also be incubated overnight in 1M HCl and recovers activity when washed with a neutral or basic buffer.

Example 4

A Second Binding Site in at the Interface of U09'

Figure 7:
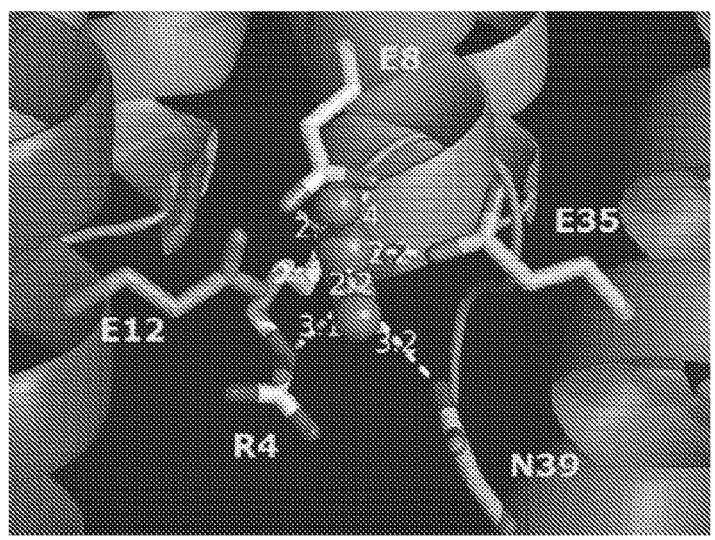
FIG. 7. Schematic shows the second binding site identified at protein interfaces in the crystal structure, explaining the multiple binding events indicated for the protein.

It is further noted that the U09-based proteins can have a second uranyl-binding site. When uranyl binding of the original U09' construct was tested using competition with the carbonate ligand, it was noted that the peak was broad (FIG. 6), indicating multiple unique binding events. The protein was crystallized and it was found that, in addition to the designed site, the uranyl cation also occupied a second site defined by equatorial E8, E12, and E35 from three monomers (FIG. 7). The site was also defined by two hydrogen bond donations to one uranyl-oxo ligand by R4 and N39.

Each equatorial ligand of the interface site (E8, E12, E35) was mutated to alanine and glutamine and each mutant tested to determine its $K_D$ (Table 1). An equatorial carboxylate ligand of the designed site (D68) was also mutated to alanine and the corresponding amine and each mutant tested to determine $K_D$. Each mutation to the corresponding ligand resulted in drastic decreases in the uranyl binding efficiency of the protein, indicating that even with the relatively mild glutamate to glutamine mutations, some amount of global change to the protein structure decreases the efficacy of both sites. Each interface site ligand was then mutated to aspartate, assuming the change in polarity in the other mutants must have caused global structure changes that affected both sites. These new mutants had binding efficiencies similar to U09', supporting the designed site as responsible for the high binding efficiency.

TABLE 1

Neither the interface nor design site mutations yield proteins with similar dissociation constants, suggesting global structure change affecting both sites for each mutation.

| Mutation | Affinity |
| --- | --- |
| E8A | 3.2 nM |
| E12A | 2.3 nM |
| E35A | 4.0 nM |
| E8Q | 4.6 nM |
| E12Q | 3.1 nM |
| E35Q | 6.7 nM |
| D68A | 3.1 nM |
| U09' | 6.9 pM |

Figure 8:
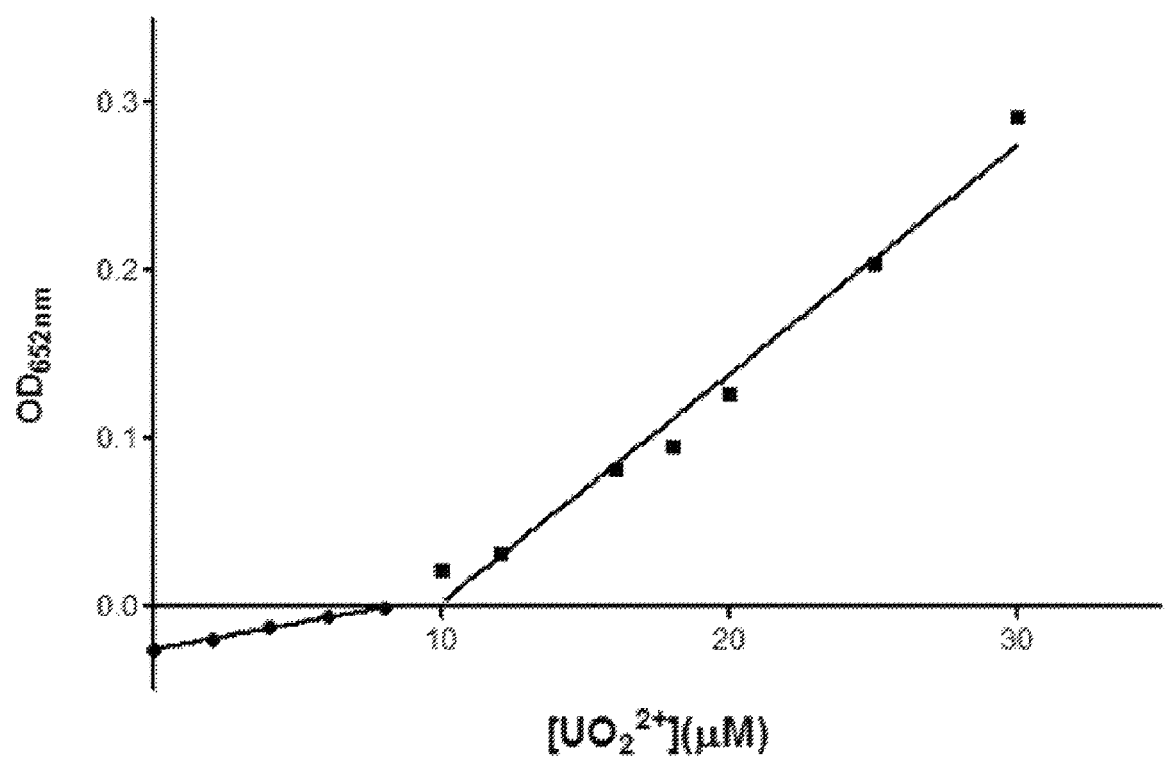
FIG. 8. Protein titration with uranyl vs. diglycolic acid (DGA). Until protein and uranyl are at a 1:1 ratio, the amount of uranyl bound by the DGA goes up slowly. Once protein and uranyl are equimolar, much more uranium is bound by the DGA and measured, indicating a 1:1 binding ratio.

To verify that the designed binding site was responsible for the high binding affinity 10 μM protein was mixed with 10 μM DGA and titrated in increasing amounts of uranyl (FIG. 8). Below 10 μM of uranyl, very little uranyl is speciated to the DGA. Above 10 μM, much more uranyl is bound by the DGA indicating a 1:1 binding ratio and suggesting the designed site is the source of the high affinity binding.

Example 5

Resin Based Enrichment with Designed Protein U09"

Figure 9:
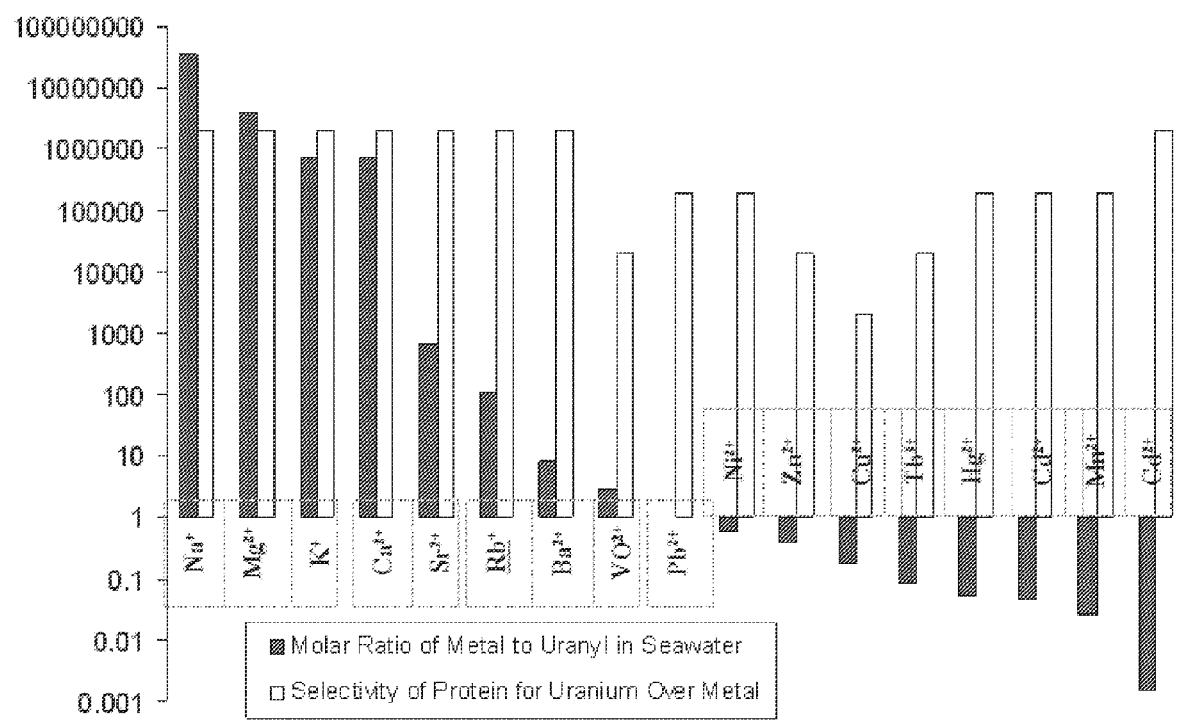
FIG. 9. Graph shows the molar selectivity of U09" for uranium. The shaded bars correspond with the molar excess or derth of a given ion compared with uranium. The ivory bars correspond with the selectivity of U09" over a given metal. The line at $2 \times 10^6$ corresponds to the limit of detection for selectivity. Any metal having selectivity reported as $2 \times 10^6$ should be understood to have selectivity greater than or equal to $2 \times 10^6$.

Since U09" exhibits a high binding affinity to uranyl, its selectivity of uranyl over other metal ions was examined and uranyl enrichment from seawater was tested using this protein. The protein was immobilized on a resin. Eighteen metal ions relevant to extraction from seawater and competition with uranyl were competed against uranyl for protein binding (FIG. 9). The Arsenazo III method (21) was used to detect uranyl. For these tests a maximum ratio of $2.0 \times 10^6$ metal ions to 1 uranyl ion was used. If no uranyl was detected, the competition was tested again with metal diluted ten-fold and repeated until uranyl was detected. Most ions were not able to out-compete uranyl, even at $2.0 \times 10^6$ fold excess. Of those ions that did compete, none competed at low enough levels to interfere with binding to uranyl in seawater. For instance, calcium(II) is present at 10 mM in seawater, but U09" showed a $2.0 \times 10^6$-fold selectivity to uranyl over calcium(II). Such a high selectivity for uranyl across such a wide range of metals appears to be unprecedented for proteins.

Example 6

U09" May Bind One Equivalent of Uranyl or 1:1 Uranyl-Carbonate

Figure 10:
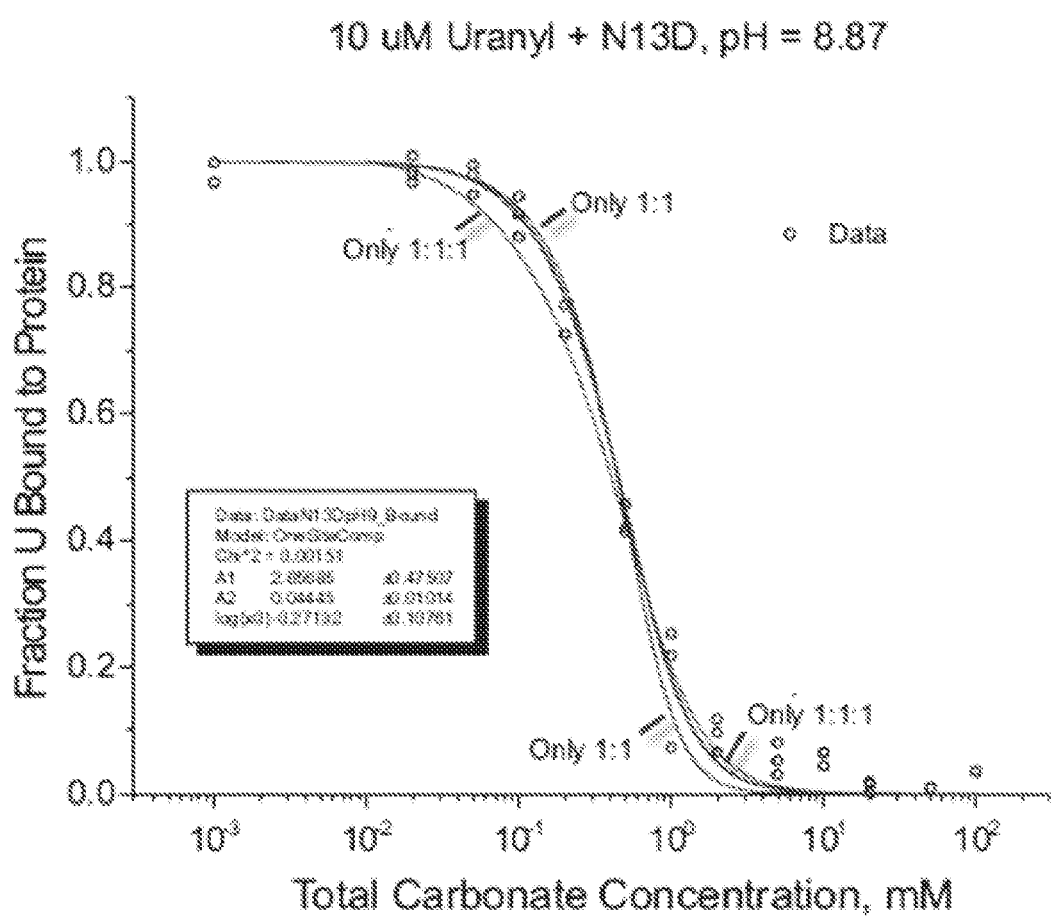
FIG. 10. Graph shows data fit to a uranyl carbonate model vs. a uranyl model. The data fits suggest models that the protein can bind one uranyl, one uranyl mono-carbonate (1:1:1), or both uranyl (1:1) and uranyl mono-carbonate (1:1:1).

Although the protein was initially designed to bind one equivalent of uranyl, the possibility remains that U09" instead binds one equivalent of a 1:1 uranyl-carbonate complex (FIG. 10), as suggested by data fitting. Binding the uranyl-carbonate complex or a mixture of uranyl and uranyl-carbonate would decrease the affinity necessary for sea water enrichment. This may present a different strategy to enrich uranyl from seawater: binding uranyl-monocarbonate with protein.

Example 7

Cell-Based Enrichment with Designed Protein U09"

Figure 11:
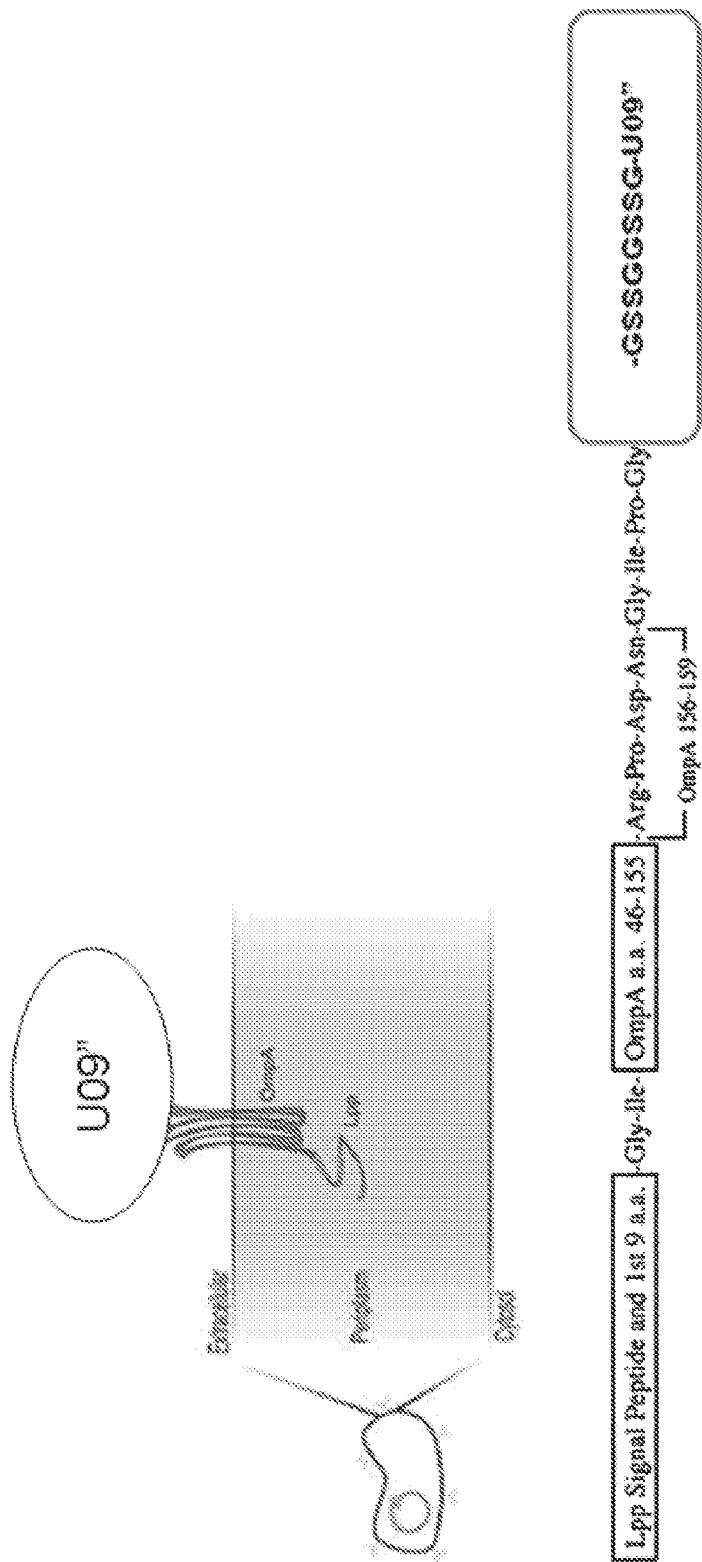
FIG. 11. Schematic shows a strategy for cell surface display of protein. U09" is fixed to a truncated OmpA with a membrane localization tag. The truncation is located so that U09" is displayed outside the cell. The amino acid linker between OmpA and U09"shown in the figure is provided as SEQ ID NO: 3.
Figure 12:
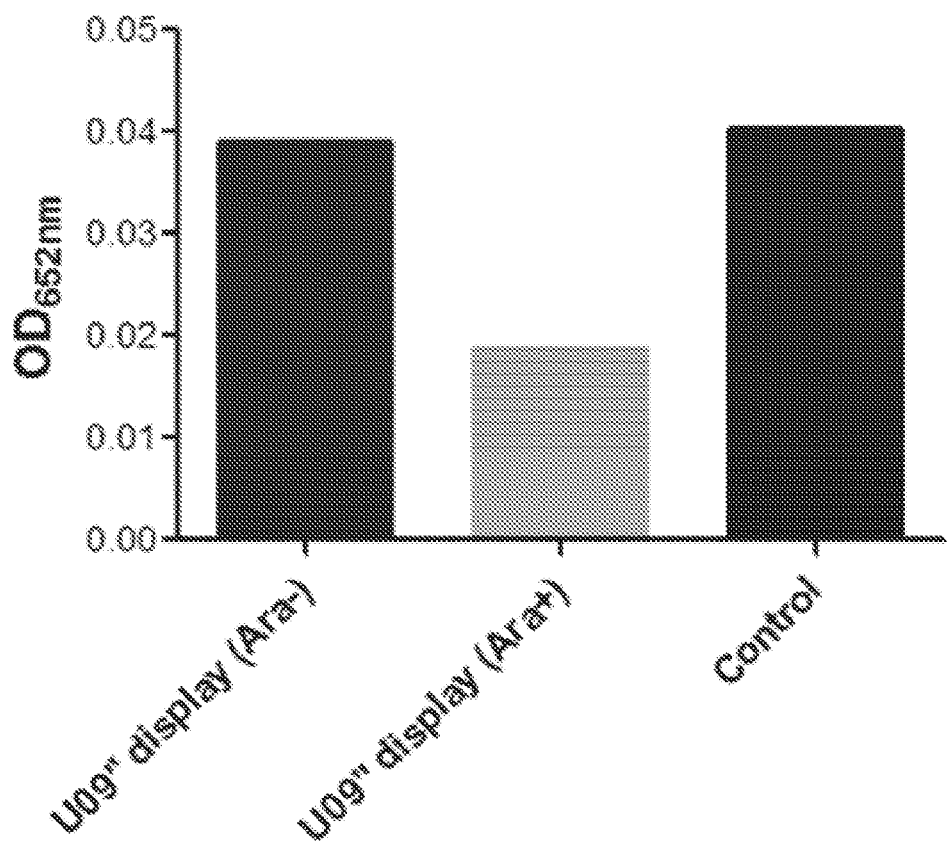
FIG. 12. Graph shows enrichment using cell surface displayed protein. The first column is the pBAD cell line containing the OmpA-fusion protein without induction. The second column is the same line with overnight induction. The final column is the concentration of uranyl in the solution with cells. While cells not induced are not able to enrich uranium, induced cells are able to enrich half of the uranium from a pH 9 solution with 20 mM carbonate, indicating a free uranyl concentration and $K_D$ of around $1.7 \times 10^{-20}$ M when immobilized on the cell surface.

In addition to resin based enrichment, methods were developed for cell surface display to develop cell-based enrichment strategies. An OmpA-U09" fusion protein was cloned into a pBAD vector under control of and arabinose induced promoter region (FIG. 11). Each time protein was grown to $OD_{600}$=0.4-0.8 and induced with arabinose. It was found that overnight induction at 37° C. with 2% m/v arabinose induction to gave the best results for expression. Cells were harvested the next morning by centrifugation at 3000 rpm for 10 minutes. Cells were normalized to 1 mL of $OD_{600}$=5 solutions and tested by mixing cells with 20 mM carbonate in 10 mM pH 9.0 Tris buffer with 300 mM NaCl. Controls of cells not induced and concentration without cells were performed (FIG. 12). While cells not induced were not able to enrich uranium, induced cells are able to enrich half of the uranium from a pH 9 solution with 20 mM carbonate, indicating a free uranyl concentration (and therefore $K_D$) of around $1.7 \times 10^{-20}$ when immobilized on the cell surface. Preliminary result indicate that the majority of uranyl from synthetic seawater can be enriched with this construct.

Example 8

Materials and Methods

Mutation, Expression and Purification of Protein
U09 gene was synthesized by GeneScript as shown below:

```
L   D   C   R   E   R   T   E   K   D   L   E   N   L   E   K   E   L   M   E
CTG GAT TGC CGT GAA CGC ATT GAA AAA GAC CTG GAA AAC CTG GAA AAA GAA CTG ATG GAA   20

M   K   S   I   K   L   S   D   D   E   E   A   V   V   E   R   A   L   N   Y
ATG AAA AGC ATC AAA CTG TCT GAT GAC GAA GAA GCG GTG GTT GAA CGT GCC CTG AAT TAT   40

R   D   D   S   V   Y   Y   L   E   K   G   D   H   I   T   S   F   G   C   I
CGC GAT GAC ACT GTC TAT TAC CTG GAA AAA GGC GAT CAT ATT ACC TCC TTT GGT TGT ATC   60

T   Y   A   Q   G   L   L   D   S   L   R   M   L   H   R   I   I   E   G
ACG TAC GCG CAG GGC CTG CTG GAT AGC CTG CGT ATG CTG CAC CGC ATT ATC GAA GGT       79
```

Certain positions that were identified as having a role in uranyl binding a indicated in bold underline [SEQ ID NO:1 (protein); SEQ ID NO: 2 (polynucleotide)].
U09" gene after transformations:

```
L   D   C   R   E   R   I   E   K   D   L   E   D   L   E   K   E   L   M   F
CTG GAT TGC CGT GAA CGC ATT GAA AAA GAC CTG GAA GAC CTG GAA AAA GAA CTG ATG GAA   20

M   K   S   I   K   L   S   D   D   E   E   A   V   V   E   R   A   L   N   Y
ATG AAA AGC ATC AAA CTG TCT GAT GAC GAA GAA GCG GTG GTT GAA CGT GCC CTG AAT TAT   40

R   D   D   S   V   Y   Y   L   E   K   G   D   H   I   T   S   F   G   C   I
CGC GAT GAC AGT GTC TAT TAC CTG GAA AAA GGC GAT CAT ATT ACC TCC TTT GGT TGT ATC   60

T   Y   A   E   G   L   T   D   S   L   R   M   L   H   R   I   I   E   G
ACG TAC GCG GAG GGC CTG ACG GAT AGC CTG CGT ATG CTG CAC CGC ATT ATC GAA GGT       79
```

[SEQ ID NO:3 (protein); SEQ ID NO: 4 (polynucleotide)]

Mutations were performed using Pfu Ultra II polymerase from Agilent. U09 and all mutations were cloned and expressed in pMCSG19 vector for expression in PRK1037 *E. coli* as previously described (1). All plasmid DNA was purified using a spin mini-prep kit, eluted into Type A water. Protein was induced at OD=0.6 with 1 mM IPTG and cells were grown overnight at room temperature before harvesting. Cells were lysed by sonication in the presence of 100 μM PMSF as serine protease inhibitor. Supernatant was separated by centrifugation and filtration through 0.45 μm PVDF. Ni-NTA columns were run using 10 mM Tris pH 7.4 with 300 mM NaCl and imidizole ramping from 0 to 500 mM. Ni-NTA column chromatography gave pure protein in good yields. Protein samples were concentrated using 10 kDa cutoff centrifuge filters and desalted into appropriate buffers. All crystallization samples were further purified by gel filtration. Gel filtrations were run in 10 mM Tris pH 7.4 with 100 mM NaCl.

Arsenazo III Determination of Uranyl

A modification Arsenazo III method (23) was employed to determine uranyl concentrations unless otherwise indicated. 50 μL of 80 μM Arsenazo III at pH 1 was titrated with equal volume of uranyl solutions ranging from 0 to 10 μM, and the absorbance at 652 nm was monitored. Absorbance at 652 nm increase linearly in this range, and can be converted to uranyl concentrations. For high DGA or carbonate concentrations HCl was added to final Arsenazo solution to compensate for buffering activity of carboxylates.

DGA Competition Assays

DGA competition assays were performed at pH 8.0 in 10 mM Tris buffer with 300 mM NaCl. Standard solutions of 100 μM protein and 100 uM $UO_2^{2+}$ were prepared and diluted 10 fold with the appropriately scaled DGA buffer to give final concentrations as shown. Solution was mixed and filtered through 10 kDa cutoff centrifuge filters. Flow-through was tested for uranyl concentration.

Carbonate Competition Assays

Carbonate competition assays were performed by mixing protein with pH 8.0 10 mM Tris buffer with 300 mM NaCl and various concentrations of carbonate. Uranyl was mixed in to yield the reported final concentrations of each species. Solutions were tested in the same manner as DGA assays.

Resin Immobilized U09 Mutants

Protein was immobilized on Sulfhydryl Coupling Resin from G-Biosciences® following the suggested procedure. Resin immobilized proteins were tested with carbonate assays, but spun through silica spin columns as opposed to 10 kDa cutoff filters. Again, flow-through was tested for uranyl concentration.

Seawater Extractions

Synthetic seawater was created according to accepted protocol, (23) with 13.4 nM added uranyl. Resin was incubated with seawater for 30 minutes before seawater was removed. Resin was washed with 10 mM pH 9.0 Tris before uranyl was eluted from resin in five fractions of 100 uL of 50 mM carbonate in 10 mM pH 9.0 Tris and each tested with Arsenazo III for uranyl.

Example 9

Additional Uranyl Binding Protein Coding Sequences

The sequences of additional uranyl binding proteins U02, U04 and U10 (see FIG. 1) were also analyzed to determine which residues were involved uranyl binding and which residues could be further substituted to enhance the binding properties.

```
U02
                                                   (SEQ ID NO: 5)
SGGGGEHQHG EEMMAAVPAP DAEGAAGFDE FPIGEDRDVG PLHVGGVYFQ PVEMHPAPGA    60

QPSKEEADCH IEAQIHANEA GKDLGYGVGD FVPYLRVVAF LQKHGSEVKQ KVMFAPMNQG  120

DGPHYGANVK FEEGLGTYKV RFEIAAPSHD EYSLHIDEQT GVSGRFWSEP LVAEWDDFEW  180

KGPQW                                                              185
```

Residues involved in uranyl coordination include: E72, Q74, Q119, and D121. Additional residues that may be mutated to enhance binding include: E30R, V52T, Q74E, Q119E.

```
U04
                                                   (SEQ ID NO: 7)
ADTLLILGDS DSAGYRMSAS AAWPALLNDK WQSKTSVVNA SISGDTSQQG LARLPALLKQ   60

HQPRWVLVEL GENDGLRGFQ PQQTEQTLRQ ILQDVKAANA EPLLMQIRPP ANYGRRYNEA  120

FSAIYPNLAK EFDVPLLPFF MEEVYLKPQW MQDDGDHPNR DAQPFIADWM AKQLQPLVNH  180

DSLE                                                               184
```

Residues involved in uranyl coordination include: D11 E72 and D156 (bold). Additional residues that may be mutated to enhance binding include: F139Y (bold with underline).

```
U10
                                                   (SEQ ID NO: 9)
MSDLDTPTPS PHPVLLNLEQ FLPYRLEVLS NRISGNIAKV YGDRYGMADP EWDVITILAL   60

YPGSSASEVS DRTAMDKVAV SRAVARLLER GFIRRETHGD DRRRSMLALS PAGRQVYETV  120

APLVNEMEQR LMSVFSAEEQ QTLERLIDRL AKDGLPRMAS KD                     162
```

Residues involved in uranyl coordination include: D49 D53 and E27 (bold). Additional residues that may be mutated to enhance binding include: M75S, M75N, M75Q, and S34N (bold with underline).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Aisen, P., Leibman, A., Zweier, J. Stoichiometric and Site Characteristics of the binding of Iron to Human Transferrin. J. Biol. Chem. 253, 1930-1937 (1978).
2. Bancil, L., Bertinil, I., Ciofi-Baffonil, S., Korzyreval, T., Zovo, K., Palumaa, P. Affinity gradients drive copper to cellular destinations Nature 465, 367-368 (2010).
3. Regan, L., DeGrado, W. F. Characterization of a Helical Protein Designed from First Principles. Science 241, 976-978 (1988).
4. Lovejoy, B., Choe, S., Cascio, D., McRorie, D. K., DeGrado W. F., Eisenberg, D. Crystal structure of a synthetic triple-stranded alpha-helical bundle. Science 259, 1288-1293 (1993).
5. Iranzo, O., Ghosh, D., Pecoraro, V. L. Assessing the Integrity of Designed Homomeric Parallel Three-Stranded Coiled Coils in the Presence of Metal Ions. Inorg. Chem. 45, 9959-9973 (2006).
6. Wendt, H., Berger, C., Baici, A., Thomas, R. M., Bosshard, H. R. Kinetics of Folding of Leucine Zipper Domains. Biochemistry 34, 4097-4107 (1995).
7. Pordea, A., Ward, T. R Artificial Metalloenzymes: Combining the Best Features of Homogenous and Enzymatic Catalysis. Synlett. 20, 3225-3236 (2009).
8. DeGrado. W. F.; Summa, C. M.; Pavone, V.; Nastri, F. & Lombardi, A. De Novo Design and Structural Characterization of Proteins and Metalloproteins. Annu. Rev. Biochem. 68, 779-819 (1999).
9. Dutton, P. L., Moser, C. C., Engineering enzymes. Faraday Discuss. 148, 443-448 (2011).
10. Azoitei, M. L, Correia, B. E., Ban, Y. A., Carrico, C., Kalyuzhniy, O., Chen, L., Schroeter, A., Huang, P., McLellan, J. S., Kwong, P. D., Baker, D., Strong, R. K., Schief, W. R. Computation-Guided Backbone Grafting of a Discontinuous Motif onto a Protein Scaffold. Science 334, 373-376 (2011).
11. Touw, D. S., Nordman, C. E., Stuckey, J. A., Pecoraro, V. L. Identifying important structural characteristics of arsenic resistance proteins by using designed three stranded coils. Proc. Natl. Acad. Sci. 104, 11969-11974.
12. Matzapetakis, M., Pecoraro, V. L. Site-Selective Metal Binding by Designed Helical Peptides. J. Am. Chem. Soc. 127, 18229-18233 (2005).
13. Radford, R. J., Brodin, J. D., Salgado. E. N., Tezcan, A. Expanding the utility of proteins as platforms for coordination chemistry. Coord. Chem. Rev. 225, 790-803.
14. Lu, Y., Yeung, N., Sieracki, N., Marshall, N. M. Design of functional metalloproteins. Nature 460, 855-862 (2009).
15. Franczyk, T. S.; Czerwinski, K. R.; Raymond, K. N. Stereognostic Coordination Chemistry. 1. The Design and Synthesis of Chelators for the Uranyl Ion. J. Am. Chem. Soc. 114, 8138-8146 (1992).
16. Gordon, A. E.; Xu, J.; Raymond, K. N.; Durbin. P. Rational Design of Sequestering Agents for Plutonium and Other Actinides. Chem. Rev. 103, 4207-4282 (2003).
17. Wegner, S. V.; Boyaci, H.; Chen, H.; Jensen. M. P.; He, C. Engineering A Uranyl-Specific Binding Protein from NikR. Angew. Chem. Int. Ed. 48, 2339-2341 (2009).
18. Lee, J. H., Wang, Z., Liu, J., Lu, Y. Highly Sensitive and Selective Colorimetric Sensors for Uranyl (UO22+): Development and Comparison of Labeled and Label-Free DNAzyme-Gold Nanoparticle Systems. J. Am. Chem. Soc. 130, 14217-14226 (2008).
19. LeClainche, L., Vita, C. Selective binding of uranyl cation by a novel calmodulin peptide. Environ. Chem. Lett. 4, 45-49 (2006).
20. Zeikus, J. G.; Wolee, R. S. *Methanobacterium thermoautotrophicus* sp. n., an Anaerobic, Autotrophic, Extreme Thermophile. J Bacteriol. 109, 707-715 (1972).
21. Rohwer, H., Rheeder, N., Hosten, E. Interactions of Uranium and thorium with arsenazo III in an aqueous medium. Anal. Chim. Acta 341, 263-268 (1997).
22. Georgiou, G., Stephens, D. L., Stathopoulos, C., Poetschke H. L., Mendenhall, J., Earhart, C. F. Display of beta-lactamase on the *Escherichia coli* surface: outer membrane phenotypes conferred by Lpp'-OmpA'-beta-lactamase fusions. Protein Eng. 9, 239-247 (1996).
23. Saito, K., Miyauchi, T. Chemical Forms of Uranium in Artificial Seawater. J. Nucl. Sci. Technol. 19, 145-150 (1982).

The invention claimed is:

1. A recombinant polypeptide comprising an amino acid sequence at least 80% identical to SEQ ID NO: 1 wherein the amino acid sequence comprises one or more of the following features:
   a) an amino acid with a negatively charged side chain at the position corresponding to Asn 13 of SEQ ID NO:1;
   b) an amino acid with a negatively charged side chain at the position corresponding to Glu 17 of SEQ ID NO:1;
   c) an amino acid with a negatively charged side chain at the position corresponding to Gln 64 of SEQ ID NO:1; or
   d) an amino acid with a polar side chain at the position corresponding to Leu 67 of SEQ ID NO:1.

2. The polypeptide of claim 1, wherein the amino acid sequence comprises an amino acid with a negatively charged side chain at one or more of the positions corresponding to:
   e) Glu 8 of SEQ ID NO:1;
   f) Glu 12 of SEQ ID NO:1;
   g) Glu 35 of SEQ ID NO:1; or
   h) Asp 68 of SEQ ID NO:1.

3. The polypeptide of claim 1, wherein the polypeptide comprises at least two of said features.

4. The polypeptide of claim 1, wherein the polypeptide comprises an amino acid sequence at least 85% identical to SEQ ID NO: 1 or 3.

5. The polypeptide of claim 1, wherein the amino acid sequence comprises an Asp residue at the position corresponding to Asn 13 of SEQ ID NO: 1.

6. The polypeptide of claim 1, wherein the amino acid sequence comprises a Glu residue at the position corresponding to Glu 17 of SEQ ID NO: 1.

7. The polypeptide of claim 1, wherein the amino acid sequence comprises a Glu residue at the position corresponding to Gln 64 of SEQ ID NO: 1.

8. The polypeptide of claim 1, wherein the amino acid sequence comprises a Thr residue at the position corresponding to Leu 67 of SEQ ID NO: 1.

9. The polypeptide of claim 1, wherein the polypeptide comprises the amino acid sequence of SEQ ID NO: 1.

10. The polypeptide of claim 1, wherein the polypeptide comprises the amino acid sequence of SEQ ID NO: 3.

11. A method for binding uranyl comprising:
    (a) contacting a solution comprising uranyl with a polypeptide comprising an amino acid sequence at least about 80% identical to SEQ ID NO: 1 or 3, thereby binding the uranyl to the polypeptide.

12. The method of claim 11, wherein the solution comprises uranyl having a $^{238}U$, $^{235}U$ or $^{233}U$ uranium isotope.

13. The method of claim 11, wherein the solution comprises carbonate.

14. The method of claim 11, wherein the polypeptide binds to uranyl with a $K_D$ of between about 1.8 nM and about 1.0 fM.

15. The method of claim 11, further comprising isolating or concentrating the polypeptide bound to uranyl.

16. The method of claim 11, further comprising eluting uranyl from the polypeptide.

17. The method of claim 16, wherein eluting comprises heating the polypeptide.

18. A method for reducing the level of uranium in a solution comprising:
    (a) contacting a solution comprising uranyl with the polypeptide of claim 1 thereby binding the uranyl to the polypeptide; and
    (b) purifying the polypeptide away from the solution thereby reducing the level of uranium in the solution.

19. A method for binding uranyl comprising:
    (a) contacting a solution comprising uranyl with the polypeptide of claim 1, thereby binding the uranyl to the polypeptide.

20. The method of claim 19, wherein the polypeptide binds to uranyl with a $K_D$ of between about 100 nM and about 0.1 fM.

* * * * *

SEQUENCE LISTING

<160> NUMBER OF SEQ ID NOS: 10

<210> SEQ ID NO 1
<211> LENGTH: 79
<212> TYPE: PRT
<213> ORGANISM: Artificial Sequence
<220> FEATURE:
<223> OTHER INFORMATION: Synthetic peptide

<400> SEQUENCE: 1

```
Leu Asp Cys Arg Glu Arg Ile Glu Lys Asp Leu Glu Asn Leu Glu Lys
1               5                   10                  15

Glu Leu Met Glu Met Lys Ser Ile Lys Leu Ser Asp Ala Glu Glu Ala
            20                  25                  30

Val Val Glu Arg Ala Leu Asn Tyr Arg Asp Asp Ser Val Tyr Tyr Leu
                35                  40                  45

Glu Lys Gly Asp His Ile Thr Ser Phe Gly Cys Ile Thr Tyr Ala Gln
        50                  55                  60

Gly Leu Leu Asp Ser Leu Arg Met Leu His Arg Ile Ile Glu Gly
65                  70                  75
```

<210> SEQ ID NO 2
<211> LENGTH: 237
<212> TYPE: DNA
<213> ORGANISM: Artificial Sequence
<220> FEATURE:
<223> OTHER INFORMATION: Synthetic primer

<400> SEQUENCE: 2

```
ctggattgcc gtgaacgcat tgaaaaagac ctggaaaacc tggaaaaaga actgatggaa    60
atgaaaagca tcaaactgtc tgatgacgaa gaagcggtgg ttgaacgtgc cctgaattat   120
cgcgatgaca gtgtctatta cctggaaaaa ggcgatcata ttacctcctt tggttgtatc   180
acgtacgcgc agggcctgct ggatagcctg cgtatgctgc accgcattat cgaaggt     237
```

<210> SEQ ID NO 3
<211> LENGTH: 79
<212> TYPE: PRT
<213> ORGANISM: Artificial Sequence
<220> FEATURE:
<223> OTHER INFORMATION: Synthetic peptide

<400> SEQUENCE: 3

```
Leu Asp Cys Arg Glu Arg Ile Glu Lys Asp Leu Glu Asp Leu Glu Lys
1               5                   10                  15

Glu Leu Met Glu Met Lys Ser Ile Lys Leu Ser Asp Asp Glu Glu Ala
            20                  25                  30

Val Val Glu Arg Ala Leu Asn Tyr Arg Asp Asp Ser Val Tyr Tyr Leu
                35                  40                  45

Glu Lys Gly Asp His Ile Thr Ser Phe Gly Cys Ile Thr Tyr Ala Glu
        50                  55                  60

Gly Leu Thr Asp Ser Leu Arg Met Leu His Arg Ile Ile Glu Gly
65                  70                  75
```

<210> SEQ ID NO 4
<211> LENGTH: 237
<212> TYPE: DNA
<213> ORGANISM: Artificial Sequence
<220> FEATURE:
<223> OTHER INFORMATION: Synthetic primer

<400> SEQUENCE: 4

```
ctggattgcc gtgaacgcat tgaaaaagac ctggaagacc tggaaaaaga actgatggaa    60
atgaaaagca tcaaactgtc tgatgacgaa gaagcggtgg ttgaacgtgc cctgaattat   120
cgcgatgaca gtgtctatta cctggaaaaa ggcgatcata ttacctcctt tggttgtatc   180
acgtacgcgg agggcctgac ggatagcctg cgtatgctgc accgcattat cgaaggt     237
```

<210> SEQ ID NO 5
<211> LENGTH: 185

```
<212> TYPE: PRT
<213> ORGANISM: Artificial Sequence
<220> FEATURE:
<223> OTHER INFORMATION: Synthetic peptide

<400> SEQUENCE: 5

Ser Gly Gly Gly Gly Glu His Gln His Gly Glu Glu Met Met Ala Ala
1               5                   10                  15

Val Pro Ala Pro Asp Ala Glu Gly Ala Ala Gly Phe Asp Glu Phe Pro
            20                  25                  30

Ile Gly Glu Asp Arg Asp Val Gly Pro Leu His Val Gly Gly Val Tyr
        35                  40                  45

Phe Gln Pro Val Glu Met His Pro Ala Pro Gly Ala Gln Pro Ser Lys
    50                  55                  60

Glu Glu Ala Asp Cys His Ile Glu Ala Gln Ile His Ala Asn Glu Ala
65                  70                  75                  80

Gly Lys Asp Leu Gly Tyr Gly Val Gly Asp Phe Val Pro Tyr Leu Arg
                85                  90                  95

Val Val Ala Phe Leu Gln Lys His Gly Ser Glu Lys Val Gln Lys Val
            100                 105                 110

Met Phe Ala Pro Met Asn Gln Gly Asp Gly Pro His Tyr Gly Ala Asn
        115                 120                 125

Val Lys Phe Glu Glu Gly Leu Gly Thr Tyr Lys Val Arg Phe Glu Ile
    130                 135                 140

Ala Ala Pro Ser His Asp Glu Tyr Ser Leu His Ile Asp Glu Gln Thr
145                 150                 155                 160

Gly Val Ser Gly Arg Phe Trp Ser Glu Pro Leu Val Ala Glu Trp Asp
                165                 170                 175

Asp Phe Glu Trp Lys Gly Pro Gln Trp
            180                 185

<210> SEQ ID NO 6
<211> LENGTH: 558
<212> TYPE: DNA
<213> ORGANISM: Artificial Sequence
<220> FEATURE:
<223> OTHER INFORMATION: Synthetic primer

<400> SEQUENCE: 6
ggttctggcg gtggcggtga acatcagcac ggcgaagaaa tgatggcggc cgtgccggca      60
ccggatgctg aaggtgcagc tggctttgac gaatttccga ttggtgaaga tcgtgacgtg     120
ggtccgctgc atgtcggcgg tgtgtatttt cagccggttg aaatgcaccc ggcaccgggt     180
gcccaaccgt caaaagaaga agcggattgc atattgaag cccagatcca cgcaaacgaa      240
gctggcaaag atctgggcta tggtgtgggc gactttgttc cgtacctgcg cgtggttgcg     300
tttctgcaaa aacatggttc ggaaaaagtt caaaaagtca tgttcgcacc gatgaaccaa     360
ggtgatggcc cgcactatgg cgctaatgtt aaatttgaag aaggtctggg cacctacaaa     420
gtccgtttcg aaattgcggc cccgagccat gatgaatact ctctgcacat cgacgaacag     480
acgggtgtca gtggccgctt ttggtccgaa ccgctggttg cggaatggga tgacttcgaa     540
tggaaaggtc cgcaatgg                                                   558

<210> SEQ ID NO 7
<211> LENGTH: 184
<212> TYPE: PRT
<213> ORGANISM: Artificial Sequence
<220> FEATURE:
```

<223> OTHER INFORMATION: Synthetic peptide

<400> SEQUENCE: 7

Ala Asp Thr Leu Leu Ile Leu Gly Asp Ser Asp Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
            35                  40                  45

Gln Gly Leu Ala Arg Leu Pro Ala Leu Leu Lys Gln His Gln Pro Arg
        50                  55                  60

Trp Val Leu Val Glu Leu Gly Glu Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Pro Pro Ala Asn
            100                 105                 110

Tyr Gly Arg Arg Tyr Asn Glu Ala Phe Ser Ala Ile Tyr Pro Lys Leu
            115                 120                 125

Ala Lys Glu Phe Asp Val Pro Leu Leu Pro Phe Phe Met Glu Glu Val
        130                 135                 140

Tyr Leu Lys Pro Gln Trp Met Gln Asp Asp Gly Asp His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180

<210> SEQ ID NO 8
<211> LENGTH: 552
<212> TYPE: DNA
<213> ORGANISM: Artificial Sequence
<220> FEATURE:
<223> OTHER INFORMATION: Synthetic primer

<400> SEQUENCE: 8
gcggataccc tgctgattct gggcgatagc gacagcgcgg gctatcgtat gagtgcttcc      60
gcggcctggc cggcactgct gaacgataaa tggcagagca aaacctctgt ggttaatgcg    120
tcaatctcgg gcgacacgag tcagcaaggt ctggcacgtc tgccggctct gctgaaacag    180
catcaaccgc gctgggtcct ggtggaactg ggcgaaaacg atggcctgcg tggttttcag    240
ccgcagcaaa ccgaacagac gctgcgccag attctgcaag acgtgaaagc agctaatgcc    300
gaaccgctgc tgatgcagat ccgtccgccg gcaaactatg gccgtcgcta caatgaagcg    360
ttttccgcca tttatccgaa actggctaaa gaatttgatg ttccgctgct gccgtttttc    420
atggaagaag tctacctgaa accgcagtgg atgcaagatg acggtgatca tccgaaccgt    480
gacgcacagc cgttcatcgc agattggatg gccaaacagc tgcaaccgct ggttaatcac    540
gacagcctgg aa                                                         552

<210> SEQ ID NO 9
<211> LENGTH: 162
<212> TYPE: PRT
<213> ORGANISM: Artificial Sequence
<220> FEATURE:
<223> OTHER INFORMATION: Synthetic peptide

<400> SEQUENCE: 9

```
Met Ser Asp Leu Asp Thr Pro Thr Pro Ser Pro His Pro Val Leu Leu
1               5                   10                  15

Asn Leu Glu Gln Phe Leu Pro Tyr Arg Leu Glu Val Leu Ser Asn Arg
            20                  25                  30

Ile Ser Gly Asn Ile Ala Lys Val Tyr Gly Asp Arg Tyr Gly Met Ala
        35                  40                  45

Asp Pro Glu Trp Asp Val Ile Thr Ile Leu Ala Leu Tyr Pro Gly Ser
    50                  55                  60

Ser Ala Ser Glu Val Ser Asp Arg Thr Ala Met Asp Lys Val Ala Val
65                  70                  75                  80

Ser Arg Ala Val Ala Arg Leu Leu Glu Arg Gly Phe Ile Arg Arg Glu
                85                  90                  95

Thr His Gly Asp Asp Arg Arg Arg Ser Met Leu Ala Leu Ser Pro Ala
                100                 105                 110

Gly Arg Gln Val Tyr Glu Thr Val Ala Pro Leu Val Asn Glu Met Glu
            115                 120                 125

Gln Arg Leu Met Ser Val Phe Ser Ala Glu Glu Gln Gln Thr Leu Glu
    130                 135                 140

Arg Leu Ile Asp Arg Leu Ala Lys Asp Gly Leu Pro Arg Met Ala Ser
145                 150                 155                 160

Lys Asp

<210> SEQ ID NO 10
<211> LENGTH: 486
<212> TYPE: DNA
<213> ORGANISM: Artificial Sequence
<220> FEATURE:
<223> OTHER INFORMATION: Synthetic primer

<400> SEQUENCE: 10
atgtcagatc tggacacccc gacgccgtcg ccgcatccgg tgctgctgaa cctggaacag        60
tttctgccgt atcgtctgga agtcctgagc aaccgcattt ctggcaatat cgcaaaagtg       120
tatggcgatc gttacggtat ggctgatccg gaatgggacg ttattaccat cctggcactg       180
tacccgggta gctctgctag tgaagtctcc gatcgcacgg cgatggacaa agtggccgtt       240
agtcgcgcgg ttgcacgtct gctggaacgt ggttttattc gtcgcgaaac ccacggtgat       300
gaccgtcgcc gtagtatgct ggcactgtcc ccggctggcc gtcaggtcta tgaaacggtg       360
gcgccgctgg ttaatgaaat ggaacaacgc ctgatgtcag ttttctcggc cgaagaacag       420
caaaccctgg aacgtctgat cgatcgcctg gcgaaagacg gtctgccgcg tatggcctct       480
aaagat                                                                 486
```